United States Patent [19]

Short et al.

[11] Patent Number: 5,137,924
[45] Date of Patent: Aug. 11, 1992

[54] CATALYTIC PROCESS

[75] Inventors: Glyn D. Short; James R. Jennings, both of Cleveland, England

[73] Assignee: Imperial Chemical Industries PLC, London

[21] Appl. No.: 758,418

[22] Filed: Sep. 3, 1991

Related U.S. Application Data

[63] Continuation of Ser. No. 625,694, Dec. 12, 1990, abandoned, which is a continuation of Ser. No. 139,838, Dec. 29, 1987, abandoned, which is a continuation of Ser. No. 559,641, Dec. 9, 1983, abandoned.

[30] Foreign Application Priority Data

| Dec. 13, 1982 | [GB] | United Kingdom | 8235418 |
| Dec. 13, 1982 | [GB] | United Kingdom | 8235434 |
| Dec. 13, 1982 | [GB] | United Kingdom | 8235443 |
| Aug. 4, 1983 | [GB] | United Kingdom | 8321118 |
| Aug. 4, 1983 | [GB] | United Kingdom | 8321120 |

[51] Int. Cl.⁵ .............................. C07C 27/06
[52] U.S. Cl. .................... 518/700; 518/701; 518/713; 518/715; 518/716
[58] Field of Search ............... 518/700, 701, 713, 715, 518/716

[56] References Cited

U.S. PATENT DOCUMENTS 1,707,331 4/1929 Storch .
2,061,470 11/1936 Larson .
3,758,417 9/1973 Magoon et al. .
4,181,630 1/1980 Baglin et al. .

FOREIGN PATENT DOCUMENTS 34011 8/1981 European Pat. Off. .

OTHER PUBLICATIONS

Wallace et al, Fifteenth Rare Earth Research Conference, University of Missouri-Rolla, Rolla, Missouri, Jun. 15-18, 1981.
Baglin et al (II) Ind. Eng. Chem Prod Res Dev (1981) 20 pp. 87-90.

Primary Examiner—Howard T. Mars
Attorney, Agent, or Firm—Cushman, Darby & Cushman

[57] ABSTRACT

Methanol synthesis over a catalyst derived from an alloy of copper and/or a platinum group metal and a highly oxidizable metal such as a rare earth metal can be carried out at unusually low temperatures such as 70° C. and using synthesis gas deficient in hydrogen. The process life of the catalyst is no longer if the starting alloy contains a further metal such as aluminum or manganese. The synthesis gas should preferably be very pure and substantially free of carbon dioxide and water vapor. The process can be advantageously carried out using the catalyst suspended in an inert liquid.

9 Claims, No Drawings

CATALYTIC PROCESS

This is a continuation of application Ser. No. 07/625,694, filed on Dec. 12, 1990, which was abandoned upon the filing hereof which was a continuation of Ser. No. 139,838 filed Dec. 29, 1987 now abandoned; and which was a continuation of Ser. No. 559,641 filed Dec. 9, 1983, now abandoned.

This invention relates to a catalytic process, particularly methanol synthesis, and to catalysts therefor.

It has been recently proposed, for example by Wallace et al (15th Rare earth research conference, Rolla-Missouri 1981) and in U.S. Pat. No. 4,181,630 to synthesise methanol over a catalyst made by forming an alloy of an active metal such as copper with a metal having a high affinity for oxygen such as a rare earth metal, Group IV A metal or actinide and oxidising the alloy in controlled conditions. Such catalysts were reported to be active at temperatures of the same order as those used in conventional copper catalysed methanol synthesis, with maximum activity at for example 270°, 290°, 320° or 340° C. depending on the composition of the catalyst.

We have now found that an alloy-derived catalyst can be usefully active in methanol synthesis at temperatures substantially lower than those so far specifically disclosed, can be treated and/or modified so as to lengthen their process life and can operate efficiently in synthesis gas of unconventional composition.

In this specification the Groups of the Periodic Table are those set out in "Abridgments of Specifications" published by the UK Patent Office.

According to the invention in its first aspect methanol synthesis by reacting carbon monoxide with hydrogen over a catalyst comprising at least one active metal and/or oxide and a difficultly reducible oxidic support material made by oxidation (as hereinafter defined) of at least one element is characterised by a catalyst temperature under 240° C.

"Oxidation" means bringing to at least that state of oxidation assumed by the element when in contact with methanol synthesis gas. As will be seen, the extent of oxidation may be relatively small, especially when the synthesis gas contains only carbon monoxide and hydrogen.

The invention in its second aspect relates to the composition of the synthesis gas. In industrial methanol synthesis it is customary to use a synthesis gas containing hydrogen in excess of what is required to react with all the carbon oxides present. Proposals have been made, for example in UK 1435253 (Karavaev et al), to use a synthesis gas deficient in hydrogen, but there has been no disclosure which of the usual methanol synthesis catalysts is satisfactory in such conditions.

According to the invention a process of methanol synthesis by reacting carbon monoxide with hydrogen over a catalyst comprising a metal and/or oxide having catalytic activity for methanol synthesis and a difficultly reducible oxidic support material made by oxidation (as herein defined) of at least one element is characterised in that the composition of the gas mixture passed over the catalyst corresponds to $$R = \frac{H_2 - CO_2}{CO + CO_2} = 0.5 \text{ to } 2.0$$

Further details of synthesis gas composition will be given below.

The invention in its third aspect provides a process of methanol synthesis over a catalyst comprising at least one active metal and/or oxide and a difficultly reducible oxidic support material made by oxidation (as herein defined) of at least one element, characterised in that the catalyst is contained in a body of liquid substantially inert in the conditions of synthesis.

The detailed conditions and advantages of this aspect will be described below.

In making the catalyst to be used in the process the oxidation is carried out preferably in the presence of the metal which will as such or as its oxide be the active material of the catalyst. (Such metal will be referred to herein as "activatable metal"). Preferably oxidation is applied to a catalyst precursor which is a compound of one or more such activatable metals with the element. The compound can include non-metals but preferably the elements present are metals and the precursor is an alloy. The term "alloy" includes all types of microscopically homogeneous metal combinations whether containing or consisting of intermetallic compounds, interstitial compounds, single or mixed crystallographic phases or amorphous material.

The active or activatable metal preferably is or includes copper and/or one or more platinum group metals having methanol synthesis activity, for example ruthenium or rhodium but especially palladium. The upper limit of the content of activatable metal is set by the need to permit oxidation of other components at a convenient rate. The content of copper is typically up to 80, preferably up to 70 and at least 5%, for example in the range 30–60 for example 40–50%, calculated by weight on the precursor from which the catalyst has been obtained. The content of the platinum group metal in the catalyst precursor is typically in the range 0.1–20, for example 1–10,% calculated as mentioned above.

When the active material comprises at least one platinum group metal the catalyst and the precursor from which it is formed are new compositions of matter, constituting a fourth aspect of the invention.

Naturally the catalyst should be substantially free of metals capable of catalysing unwanted side reactions.

The oxidic support of the catalyst and also any other oxides introduced by the oxidation can be identified with known oxides but, especially when such oxidation is by compounds of very low oxidising power, can be incompletely oxidised as in some lower valency state or contain other elements such as carbon.

The elements whose oxide is difficultly reducible to elements are preferably metals having a standard electrode potential (stable cation to metal) at least 0.8 volt negative with respect to the standard hydrogen electrode. (A table of such potentials is set out on pages D 145-6 of the CRC Handbook of Chemistry and Physics 58th edition 1977-1978, published by CRC Press, Cleveland, USA). A preferred catalyst is one obtained from a precursor alloy containing, apart from activatable metal only metals having a standard electrode potential at least 1.3 volt negative with respect to the standard hydrogen electrode. Examples of suitable metals are manganese (1.029 volts) and vanadium (1.2 volts) and, in a still preferred range above 1.8, rare earths particularly those of atomic number 62 and below, such as cerium 2.335 volts, lanthanum 2.37 volts and praseodymium, neodymium and samarium, other Group III A (including thorium), II A, IV A and V A metals. If rare earth metal is present, preferably more than one is used for example as in the available mixtures didymium or mischmetall. Preferred metals other than rare earths are aluminium, yttrium, and Group IV A metals.

A catalyst of usefully lengthened process life can be derived from a combination comprising at least two such metals, one of which is not a rare earth metal. Preferably at least one of the metals has an electrode potential above 1.8 volt negative with respect to the standard hydrogen electrode and at least one has such a potential in the range 0.8 to 1.8 volt. In making the active catalyst it is possible that the metals are oxidised to different extents, those of lower potential being less oxidised than those of higher potential. The active catalyst may contain one or more intermetallic compounds of the active metal(s) with one or more of the oxidisable metals. Typical combinations include (a) one or more rare earth metals with (b) aluminium and/or manganese. Rare earth and aluminium may be present for example in the weight ratio range 10 to 0.2, especially between 6 and 1. When manganese is a constituent of the alloy from which the catalyst is made, a preferred alloy comprises copper and rare earth metal in a weight ratio between 0.5 and 2.0 and manganese to the extent of 0.5 to 15, especially 1–5% w/w of the total alloy. Aluminium can also be present, to the extent of for example 1–20% w/w of the total alloy.

The above-mentioned catalysts containing two or more oxidic support materials and the alloys from which they are made by oxidation are believed to be new compositions of matter, and constitute a fifth aspect of the invention.

A further interesting catalyst within the scope of the invention is one containing as active material a platinum group metal and an oxide having methanol synthesis activity. Such oxides are usually reducible to metal with moderate difficulty, corresponding to a standard electrode potential between 0.5 and 0.8. Specific examples are palladium + zinc and/or chromium.

In addition to the active metal and/or oxide and the oxidic support material made by oxidation, the catalyst can contain one or more of such constituents not so obtained. These can be introduced for example by adding one or more of them to the catalyst after its formation from the precursor, or possibly by incorporation into the alloy at the melting stage. Other constituents optionally present in the catalyst are graphite (especially as a shaping lubricant), active carbon, and refractory solids such as silicon carbide or silicon nitride. An especially important purpose of such additional components is to assist in bringing the catalyst into a suitable mechanical form, for example by binding the catalyst constituents together in random packable particles (such as 2–20 mm cylinders, rings or spheres), or improving the cohesion of fluidisable particles or the adhesion of a catalyst layer to a structured ceramic or metal support or heat exchange surface.

The catalyst precursor can be made by melting or sintering together the metal components of the alloy. The melting technique depends of the metals present, an electric arc being desirable when all of them melt at over 1000° C., for example those containing zirconium or hafnium. Those containing Group II or Group III metals, including some rare earth metals, can be made at lower temperatures, for example under 1000° C. Usually it is preferred to make a homogeneous melt, but useful catalysts can be made from compositions in which alloying takes place at junctions between metal or alloy particles but not within such particles. Very convenient melting or sintering method uses radio frequency induction heating or an electron beam. Melting and subsequent solidification should be carried out in a vacuum or inert atmosphere, preferably a noble gas.

After formation of the precursor, it or the catalyst obtained from it has to be brought into a mechanical state suitable for the process to be catalysed. If desired, the molten precursor can be comminuted, for example by spraying, and may then be finely enough dispersed to be used as a feed for shaping or in a fluidised bed or in presence of a liquid. More conveniently, the solid precursor can be crushed and then, if it is to be used in a fixed catalyst bed, shaped mechanically by, for example, compression alone or with a binder or lubricant such as graphite or application to the surface of a shaped support. Such comminution or crushing steps are best carried out in an inert atmosphere, but the finely divided material can be stabilised by superficial oxidation in cool oxygen, whereafter it can be handled in air. Preferably the catalyst-forming oxidation is carried out before shaping, as that any chemical change resulting in a change in density takes place largely before shaping and thus cannot damage the shaped pieces mechanically. Especially if the precursor includes a hydride-forming metal, for example rare earth or titanium, in addition to the activatable metal and/or metal convertible to active oxide, it is preferably hydrided before comminution, to make it more fragile.

The step of hydriding before comminution results in the formation of a catalyst precursor having advantages over non-hydrided precursor, in that the catalyst resulting from it in contact with methanol synthesis gas may be found to maintain its activity for longer periods. Hydriding can be, alternatively or additionally, carried out after comminucation.

Some at least of such hydrided catalyst precursors are believed to be new compositions of matter, and thus they constitute a sixth aspect of the invention. Their general formula is, by atomic proportions

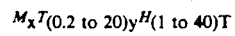

$$M_x T(0.2 \text{ to } 20) y^H (1 \text{ to } 40) T$$

where
  M is copper and/or at least one platinum group metal;
  T is selected from rare earth metals; yttrium, titanium, zirconium, hafnium and thorium;
  $x = y = 1$ when M is copper, $y = 20x$ when M is a platinum group metal.

More than one metal M or T can be present. In addition, minor proportions of metals outside these classes can be present, especially aluminium, manganese or alkaline earths.

The preferred metal combinations are as described herein for other aspects of the invention.

If desired, the hydridation can be carried out in a plurality of cycles of hydride formation followed by hydride decomposition by change of pressure and/or temperature.

Whether or not cyclic hydridation is used, hydridation of the precursor is preferably to at least 50% of its capacity. The hydrogen pressure is typically in the range 1–200 bar abs. and the temperature under 50° C.

In making the catalyst the oxidation step is preferably so as to oxidise the metal of high electrode potential, but not to oxidise in bulk the active metal. There may be slight, mainly superficial, oxidation of active metal, but this should be insufficient to produce an exotherm in subsequent reduction with hydrogen. Oxidation can be by means of diluted oxygen, at for example 0.01 to 0.5% in methane, nitrogen or a noble gas, or by an oxygen compound such as water vapour, $CO_2$ or $N_2O$, mixed if desired with an inert or noble gas or with a reducing gas to give a balance of oxidising and reducing power. When it is intended to oxidise only the metal of electrode potential at least 0.8 volts, the oxidising agent can be carbon monoxide alone or with hydrogen: in this event the controlled oxidation need not be a distinct step in making the catalyst but takes place when the alloy is contacted with methanol synthesis gas. If the oxidation is controlled so as to oxidise active metal, a final reduction is carried out before starting up methanol synthesis.

Whereas in the last decade there have been numerous reports that alloy-derived catalysts are highly active there has been no agreement as to how best to treat the alloy or to what is present in the active catalyst. For example in U.S. Pat. No. 4,181,630 treatments with air at room temperature, air at 400° C., $H_2+H_2O$ at 400° C., or $CO+3H_2$ at 400° C. are disclosed to produce a supported copper catalyst active in methanol synthesis. It has been suggested that the element having the high affinity for oxygen is converted to oxide or hydride or that at least one of the components is converted to carbide.

In investigating such catalysts containing copper we have found higher activity in methanol synthesis than has so far been published. We believe this is at least partly the result of better activation conditions, especially avoiding excessive heating of the alloy during activation.

According to the invention in its seventh aspect an alloy of an activatable metal with an element having a high affinity for oxygen is converted to active catalyst by contacting it with a reactive medium of oxidising power less than half that of air at a temperature not over 200° C.

The temperature of conversion to active catalyst is preferably below 150° C. and can be as low as 0° C. or less, provided the consequent lengthened process start-up time can be tolerated. A very suitable temperature is in the range 40°-120° C., especially for a catalyst preparation from an alloy comprising copper and one or more hydride-forming metals such as rare earth metals.

Control of temperature can be for example by means of diluent gas, heat exchange surfaces or presence of a liquid.

The oxidation activation preferably follows a pre-treatment with hydrogen, suitably at a temperature in a range suitable for the activation.

Methanol synthesis according to the invention can be carried out in conventional conditions, for example a temperature in the range 150°-450° C., a pressure up to 400 bar abs. and a space velocity such that the methanol output is in the range 0.1 to 2.0 kg per kg of catalyst per hour.

The synthesis is carried out preferably in these conditions:
Temperature: up to 220, especially up to 180° C., and offering a choice of 50-120 and 140°-180° C. to suit process design requirements;
Pressure: up to 400, especially 20-200 bar abs;
Space velocity: 1000-80,000, especially 5000-50,000 $h^{-1}$.

The ratio R of hydrogen to carbon oxides in the gas entering the synthesis catalyst can have any convenient value for example up to 4 or even up to 12 or more, but can be sub-stoichiometric. Ratio R is expressed by the formula $$R = \frac{H_2 - CO_2}{CO + CO_2}$$

Typically it is in the range 0.5 to 2.0, especially over 0.8 and very suitably in the range 1.0 to 1.8. Further, it is preferred to keep the $CO_2+H_2O$ content of the synthesis gas below 0.2, especially below 0.05, bar and, indeed, as low as practicable; in particular below 0.1, especially below 0.01 bar: then R becomes merely the $H_2:CO$ ratio.

After leaving the synthesis catalyst the reacted synthesis gas is cooled and methanol is condensed out, if methanol is to be the product of the over-all process. In preferred operating conditions such condensed-out methanol is pure enough for many uses. If greater purity is required, the condensed-out methanol need be subjected only to a simple distillation or to adsorptive purification. The synthesis process is thus very suitable for making fuel-grade methanol economically.

When the catalyst is formed from an alloy, particles of it have essentially a metallic skeleton and thus, provided excessive oxidation is avoided, can be highly resistant to attrition. Accordingly the catalysts, preferably in fine particle form, especially under 16 mesh ASTM (1000 microns) and more preferably in the range 0.1 to 100 microns, are highly suitable for use in suspension in a liquid. At the same time, since the alloy-derived catalyst particles are generally denser than particles made by reducing oxides, they are less readily entrained in the flowing synthesis gas. Further, since the alloy-derived catalysts are active at temperature lower than oxide-derived catalysts, the liquid can have a lower boiling point than was previously thought desirable. An especially useful form of this process is operated at a temperature over 100° C., for example in the range 140°-180° C., such that the rate of reaction in a fixed bed process would have been subject to pore-diffusion limitation and could not be increased by the usual expedient of decreasing the catalyst particle size because that would result in excessive resistance to gas flow.

Such a process in which the catalyst is contained in a body of liquid substantially inert in the conditions of synthesis, constitutes the third aspect of the invention, as mentioned above.

If methanol is to be the product of the process the liquid should be readily separable from methanol. Thus it preferably has a boiling point more than 5° C. different from that of methanol and in any event should not form an azeotrope with methanol. Alternatively, if the methanol is to be reacted further, for example by dehydration, conversion to hydrocarbon or etherification or esterification, the liquid should be readily separable from the products of those further reactions. Separability is of course not needed if the liquid chosen is to be a constituent of a product mixture.

Examples of suitable liquids are aliphatic, cyclaliphatic and aromatic hydrocarbons, alcohols and esters, provided they are free of ethylenic or acetylenic unsaturation.

Suitable methanol synthesis processes in presence of liquid are described in GB-A-1413929 and EP-A-34011.

The unpurified or purified methanol product or, more preferably the reacted synthesis gas as a whole, can be passed to further reactions, especially (a) dehydration of methanol to dimethyl ether catalysed by alumina or silica-treated alumina and (b) conversion of methanol and/or dimethyl ether to aromatics catalysed by a zeolite of the ZSM-5 family or to olefins catalysed by a zeolite of the FU-1, MCH or NU-3 type.

When the starting value of R is less than 2, the unreacted gas remaining after separation of methanol is rich in carbon monoxide. This gas can be recycled to the synthesis catalyst or passed to separate downstream stages of methanol synthesis and separation, until the CO content has built up to a level at which slower synthesis cannot be tolerated. Alternatively the unreacted gas can be subjected to shift and $CO_2$ removal to increase its $H_2:CO$ ratio and then passed to methanol synthesis by recycle or downstream separate stages.

Since the synthesis can operate efficiently at low $H_2:CO$ ratios it can be fed with partial oxidation gas that has been purified of catalyst poisons but has not undergone shift or hydrogen addition. Examples of gases that can be used are Koppers-Totzek gas (R=0.47), Texaco coal gas (R=0.74) and Shell-Koppers gas (R=0.47). More conveniently the $H_2:CO$ ratio can be increased by adding hydrogen, especially as described in our published European application 47596.

Despite the low temperatures at which the process can be operated, rates of methanol production are comparable with those reported to be obtained at temperatures of maximum activity in the references. We believe an important factor leading to relatively large rates of methanol formation is the purity of the gas contacting the catalyst. Thus preferably that gas contains less than 1 part in $10^6$, especially less than 1 part in $10^9$, by weight of volatile metal compounds (these are chiefly carbonyls of iron and/or nickel). Preferably the halogen content (which apparently is in combined form as hydracid or organic compounds) is less than 1 part in $10^6$, especially less than 1 part in $10^9$, by volume as equivalent HCl. Preferably the sulphur content is less than 100 parts in $10^9$ by volume as equivalent $H_2S$.

It appears to be desirable to keep the content of such impurities down to low limits during the preparation of the catalyst.

A further important factor is the content of water and/or carbon dioxide in the synthesis gas passing over the catalyst. The partial pressure of such gases is preferably low, as described above. At the same time the process conditions should be controlled to limit the access of any by-product water to the catalyst. Thus the space velocity is preferably kept high enough to limit the occurrence of water-forming reactions and/or to carry any water rapidly away from the catalyst. It appears that at the specified low temperature, and especially the preferred upper limit 220° C. and range 140° to 180° C., especially 50°-120° C., the formation of methanol is so much more rapid than that of dimethyl ether or higher oxygenated compounds that water-formation can be substantially avoided. As a result, the low temperature and high gas purity provide a "window" leading to high output of methanol pure enough for some uses without distillation.

To provide the required level of purity the synthesis gas and any gas recycled to the synthesis is subjected preferably to at least one of the following treatments, namely a molecular sieve, cold methanol (under −20° C.) or a liquid absorber of $CO_2$ and $H_2O$ such as a glycol, polyglycol or polyglycol dialkyl ether.

In the following Examples the synthesis gas was purified, before entering the synthesis reactor, by subjection to a mixture of 5 A and 13 X molecular sieves at room temperature to remove $CO_2$, $H_2O$, sulphur compounds and halogen compounds, then to copper wool at 350° C. to decompose any metal carbonyls, then to a cooler to bring it to synthesis inlet temperature.

EXAMPLE 1

A mixture of small particles of cerium metal (50 parts) and copper metal (50 parts) all by weight was melted for 20 min in vacuo ($10^{-6}$ Torr) on a cooled copper hearth by means of an electron beam, then allowed to cool. The resulting alloy ingot, a catalyst precursor, was transferred to a glove box and ground under nitrogen to the size range 600 to 850 microns, then mixed with twice its volume of 2 mm fused silica chips and charged to a laboratory externally heatable isothermal methanol synthesis reactor. The charge was heated to 150° C. in a mixture of % v/v composition $H_2$ 72+CO 28 passed over it at 50 bar abs. pressure, 40000 $h^{-1}$ volume space velocity (calculated on the copper-cerium oxide. In the synthesis gas the precursor underwent an exothermic reaction, resulting in a temperature rise to 400° C.; it is believed that a lower temperature would have sufficed to form the catalyst. Then, at the same gas flow rate and with the temperature stabilised at 150° C. the outlet gas analysed chromatographically. The content of methanol vapour was 2-2.5% v/v. The space velocity was lowered to 7000 $h^{-1}$ and the temperature raised to 175° C., giving 4.1% v/v of methanol. The outlet gas contained under 0.1% v/v of water and an undetectably low content of methane. In the liquid phase condensed from it there was, besides methanol, under 1.0% w/w of organic compounds. The catalyst was discharged and found to contain metallic copper finely dispersed on cerium oxide.

EXAMPLE 2

(a) The catalyst precursor preparation of Example 1 was repeated with the differences that 10 parts by weight of aluminium metal were present and that melting was carried out in a radio frequency induction furnace. The activation was carried out as in Example 1 but using a gas space velocity of only 20000 $h^{-1}$. This produced a temperature rise to 200° C. at about 2 h after the precursor reached 150° C. At about 24 h later the temperature was adjusted to 200° C. and held until 240 h, by which period the methanol percentage decreased and levelled out. Then the temperature was raised to 250° C. and the flow rate doubled (marked*). Thus effected a large rise in methanol percentage, followed by a further slow decrease. The temperatures and methanol percentages at various times are shown in Table 1.

(b) A corresponding catalyst containing lanthanum in place of cerium was made and tested in the same way, but without the flow rate increase.

(c) A catalyst as (a) but containing no aluminium was made and tested in the same way, except that the low temperature and high temperature test runs were carried out separately and that the flow rate was not increased.

(d) Preparation (a) was repeated using mischmetall (mainly Ce and La, minor Nd and Pr, less than 0.1% other metals) instead of pure cerium, and tested in 60 CO:40 $H_2$ synthesis gas.

TABLE 1

| Catalyst temp. °C | \multicolumn{10}{c}{Methanol % v/v in reacted gas at various times, h} | Non-MeOH organics % w/w |
|---|---|---|---|---|---|---|---|---|---|---|---|
| | 0 | 10 | 40 | 60 | 100 | 160 | 230 | 250 | 280 | 300 | |
| a 200 | — | — | 3.8 | 3.6 | 3.2 | 3.0 | 3.0 | — | — | — | under 0.25 |
| 250 | — | — | — | — | — | — | — | 7.3* | 7.0* | 6.9* | under 0.4 |
| b 200 | — | — | 5.8 | 5.0 | 4.0 | 3.3 | 3.0 | — | — | — | under 0.4 |
| 250 | — | — | — | — | — | — | 4.7 | 3.1 | 1.0 | N/A | under 0.6 |
| c 150 | 3.0 | 2.3 | 1.3 | 1.0 | 1.0 | — | — | — | — | — | under 0.7 |
| 250 | 1.7 | 3.1 | 2.6 | — | — | — | — | — | — | — | under 1.1 |
| d 200 | — | 3.7 (20 h) | — | 2.75 | 2.5 | 2.0 | — | — | — | — | N/A |

It is evident that the alumina-free catalyst c is less active initially than a, b or d and loses its activity more rapidly. Of a and b, cerium-containing catalyst a is initially less active but levels out at an activity equal to that of b. After the step increase in temperature from 200° to 250° C., a is both more active and more stable than b. Catalyst d, containing more than one rare earth oxide, is superior to c.

As in Example 1, the outlet gas contained under 0.1% v/v of water and an undetectably low content of methane. The liquid phase condensed from (a) contained less than 0.25% w/w of non-methanol organics, one third that from (c).

EXAMPLE 3

The catalyst of Example 2 (a) was tested in methanol synthesis at 200° C., 50 bar abs. pressure, space velocity 20000 h$^{-1}$ using a gas consisting of H$_2$ and CO in the ratio 55:45, purified as before. The percentage of methanol in the outlet gas was 3.5% initially, falling to 3% v/v after 72 hours operation.

As a control, a catalyst containing no aluminium but otherwise the same was tested in the same conditions. The methanol content of the outlet gas was 3.0% initially, falling to 1.0% after 72 hours operation.

EXAMPLE 4

(a) A catalyst precursor was made by melting together in a radio frequency induction furnace 100 parts of metallic copper and 100 parts of misch-metall as used in Example 2(d). It was allowed to cool, ground to a particle size of 100–500 microns and heated in air at 300° C. The product of the heat treatment was mixed with twice its volume of 2 mm fused silica granules, charged to a tubular test reactor and heated to 150° C. in hydrogen deficient methanol synthesis gas (40 H$_2$, 60 CO v/v) flowing at a space velocity of 22500 h$^{-1}$ and at a pressure of 50 bar abs. After an exotherm of about 30° C., the temperature was fixed at 150° C. The outlet gas contained methanol, in a concentration stabilised at 4.0% v/v after 8 hours operation, but undetectable H$_2$O or CO$_2$. The liquid phase condensed from the gas contained less than 1.0% of organic compounds other than methanol, and only 0.4% w/w of water.

(b) Preparation (a) was repeated with the difference that the ground alloy was oxidised in 100% carbon monoxide instead of air and then handled in oxygen free atmospheres. When contacted with the synthesis gas an exotherm of about 60° C. was observed. The synthesis activity of the catalyst was equal to that of (a), and the product purity was similar.

EXAMPLE 5

A mixture of small particles of cerium metal (50.3 parts), copper metal (48.2 parts) and manganese metal (1.5 parts), all by weight, was melted for 20 min in vacuo (10$^{-6}$ Torr) in a radio frequency induction furnace, then allowed to cool. The resulting alloy ingot was transferred to a glove box and ground under nitrogen to the size range 600 to 850 microns, then mixed with twice its volume of 2 mm silica granules and charged to a laboratory externally heatable isothermal methanol synthesis reactor. The charge was heated to 60°–65° C. in a mixture of % v/v composition H$_2$ 65+CO 35 passed over it at 50 bar abs. pressure, 20000 h$^{-1}$ volume space velocity calculated on the density of the alloy as charged. In the synthesis gas the precursor underwent no observable exothermic reaction, but after 15 h methanol was detected in the outlet gas, and the rate of production of methanol rose to over 1% and remained there for several days until the run was voluntarily stopped, as shown in Table 2.

TABLE 2

| | \multicolumn{7}{c}{Hours on line} |
|---|---|---|---|---|---|---|---|
| | 0 | 15 | 21 | 52 | 72 | 96 | 118 | 142 |
| Methanol % v/v | 0 | 0.67 | 1.23 | 1.46 | 1.25 | 1.92 | 1.23 | 1.34 |
| Space velocity × 10$^{-3}$ | 20 | 17 | 10.5 | 10.5 | 2.5 | 4 | 5 | 4.5 |
| Inlet temp. | 65 | 68 | 68 | 69 | 70 | 71 | 82 | 97 |

The decreasing space velocity as the test proceeded is attributed to disintegration of the catalyst, causing obstruction of gas flow.

It is evident that the catalyst has remarkable methanol synthesis activity at temperatures well below those previously considered necessary for methanol synthesis. The decline in activity is believed to have been at least in part due to carbon dioxide, the concentration of which was initially too small to detect in the inlet gas but rose to 0.02% after about 68 hours on line.

EXAMPLE 6

A mixture of small particles of cerium metal (50 parts), copper metal (45 parts) and palladium metal (5 parts), all by weight was melted for 20 min in vacuo (10$^{-6}$ Torr) on a cooled copper hearth by means of an electron beam, then allowed to cool. The resulting alloy ingot, a catalyst precursor, was transferred to a glove box and ground under nitrogen to the size range 600 to 850 microns, then charged to a laboratory externally heatable isothermal methanol synthesis reactor. The charge was heated to 150° C. in a mixture of % v/v composition H$_2$ 72+CO 28 passed over it at 50 bar abs. pressure, 40000 h$^{-1}$ volume space velocity. An exothermic reaction, resulting in a temperature rise to 400° C., was observed: it is believed that a lower temperature would have sufficed to form the catalyst. Then, at the same gas flow rate the temperature was raised to 250° C. and the outlet gas analysed chromatographically. The content of methanol vapour was 2% v/v. The temperature was raised to 275° C., giving 2.6% v/v of methanol, then to 300° C., giving 2.9% v/v of methanol. These percentages of methanol vapour correspond respectively to 35.7, 46.4 and 51.8 grammols of methanol per liter of catalyst per hour. Such space time yields are approximately the same as obtained using a conventional copper-zinc-alumina methanol synthesis catalyst but with $CO_2$-containing synthesis gas so that the crude methanol product contained water. Using the catalyst according to the invention the outlet gas contained only 0.1% v/v of water and an undetectably low content of methane. In the liquid phase condensed from it there was, besides methanol, under 1.0% w/w of organic compounds. The catalyst was discharged and found to contain metallic palladium and copper finely dispersed on cerium oxide.

The methanol space time yield is almost 9 times as great as that reported by Baglin et al (U.S. Pat. No. 4,181,630) using an alloy-derived catalyst containing cerium oxide (52.44% Ce as metal) and copper (47.56%). It is also more than double the best reported in European patent application 31244.

In a comparison run using conventional copper-zinc-alumina methanol synthesis catalyst in the same conditions (temperature 250° C.) as for the above catalyst according to the invention, the space time yield of methanol was only 8.0 grammols per liter of catalyst per hour.

EXAMPLE 7

Effect of Various Treatments of Catalyst Precursor

Three samples of copper-cerium alloy made as described in Example 1 and ground to the size range 600 to 650 microns were treated as follows:

A. exposed to pure dry air at room temperature for 17 days in a closed vessel;
B. exposed to nitrogen at room temperature for 17 days;
C. in the same period of 17 days subjected 12 times to a hydrogen cycle consisting of exposure to hydrogen initially at 50 bar abs. pressure until absorption of hydrogen ceased, then re-pressurising to 50 bar abs, all at room temperature.

A sample of C was analysed immediately after the last release of hydrogen pressure and found to have the atomic composition $Cu_2Ce\ H_{14}$.

The synthesis activity of each sample was tested by charging 2 ml of each to a laboratory reactor, heating it to 65°-75° C. and passing over it at 50 bar abs. pressure mixture of 33% v/v CO and 67% v/v $H_2$ purified as described in Example 1 at flow rates in the range 25-50 l h$^{-1}$. The volume percentage of methanol in the outlet gas was measured and converted to a relative activity parameter RA by the equation:

$$RA = \% \text{ methanol} \times \frac{\text{flow rate l h}^{-1}}{40} \times \frac{6}{\text{weight of catalyst}}$$

The relative activities at run times up to 40 h were as shown in Table 3.

TABLE 3

| Catalyst | Time h | | | |
|---|---|---|---|---|
| | 10 | 20 | 30 | 40 |
| A | 0.8 | 0.35 | 0.25 | 0.2 |
| B | 0.4 | 0.5 | 0.55 | 0.6 |
| C | 0.6 | 0.7 | 0.8 | 0.85 |

It is evident that the air treatment produces a catalyst of high initial activity which is, however, not maintained. On the other hand, the hydrogen pre-treatment produces a catalyst of lower initial activity which, however, increases with time and levels out at a value well above that to which the air-treated catalyst declines. The nitrogen treated catalyst is intermediate in activity and stability.

EXAMPLE 8

Synthesis in Presence of Liquid (Design)

A sample of ground catalyst precursor prepared as in Example 4 is suspended in 10 times its weight of octane and charged to a nitrogen-filled vertical reactor having a bottom run-off for catalyst suspension, a catalyst suspension feed point near its upper end, an inlet sparger for synthesis gas and an upper outlet for reacted synthesis gas. The catalyst suspension circuit includes an agitated vessel, a slurry pump and a heat exchanger, in that order, between the run-off and the feed point. The synthesis gas outlet includes a droplet separator, a feed/effluent heat exchanger, cooler and liquid methanol separator and includes means to recycle unreacted synthesis gas.

The gas circuit is closed, purged with nitrogen, then filled with methanol synthesis gas (33% v/v CO, 67% v/v $H_2$) at a pressure of 50 bar abs., which is set in circulation. The catalyst suspension is set in circulation and slowly heated to 150° C. After a few hours at this temperature the catalyst becomes active and methanol is observed to be collecting in the separator. From this time onwards the catalyst suspension heat exchanger is adjusted so as to cool the suspension instead of heating it, so as to compensate for the exothermic heat of the synthesis reaction.

As a result of the density of the catalyst, very little of it is carried overhead into the droplet separator. From time to time catalyst is allowed to settle in the agitated vessel and is drawn off therefrom and replaced by fresh catalyst.

Raw Methanol Purity

Table 4 sets out the condensate compositions for a variety of catalysts, synthesis temperatures and space velocities, all runs using synthesis gas containing 33% CO and 67% $H_2$. It is evident that the non-methanol organics level, although variable, remains low.

TABLE 4

| Catalyst | Cu:Ce 50:50 | Cu:Ce 17:83 | Cu:Ce 33:67 | Cu:Ce:Pd 49:50:1 | Cu:Ce:Mn (Ex 5) | Cu:Ce:Al 45:45:10 |
|---|---|---|---|---|---|---|
| Temp. °C. | 70 | 70 | 100 | 70 | 70 | 125 |
| ≠SV h$^{-1}$ | 40 | 40 | 40 | 40 | 20 | 20 |
| *HCO$_2$CH$_3$ | 345 | 290 | 170 | 300 | 410 | 2000 |
| AcOCH$_3$ | 925 | 70 | 115 | 140 | 650 | 160 |
| EtOH | 1100 | 600 | 505 | 440 | 1300 | 640 |
| iso-PrOH | <5 | 10 | <5 | 15 | <5 | <5 |
| n-PrOH | 5 | <5 | <5 | 5 | 10 | 15 |
| sec-BuOH | 80 | <5 | <5 | <5 | <5 | <5 |

TABLE 4-continued

| Catalyst | Cu:Ce 50:50 | Cu:Ce 17:83 | Cu:Ce 33:67 | Cu:Ce:Pd 49:50:1 | Cu:Ce:Mn (Ex 5) | Cu:Ce:Al 45:45:10 |
|---|---|---|---|---|---|---|
| iso BuOH | <5 | <5 | <5 | <5 | <5 | <5 |
| n BuOH | <5 | <5 | <5 | <5 | <5 | <5 |
| +water | 1.4 | <1.0 | <1.0 | 1.0 | 1.0 | 2.0 |

*Organics in ppm w/w
+Water in % w/w
≠ × $10^{-3}$

We claim:

1. A process for the production of methanol comprising passing, at a temperature below 240° C., and at a pressure between 20 and 120 bar abs, a synthesis gas containing carbon monoxide and hydrogen, wherein the total partial pressure of steam and carbon dioxide in the synthesis gas, if any, is below 0.1 bar, over a catalyst obtained by oxidizing, at a temperature not over 200° C., with a reactive medium of oxidizing power less than half that of air, said reactive medium selected from the group consisting of
   i) oxygen diluted with methane, nitrogen or a noble gas
   ii) nitrous oxide mixed with an inert or noble gas, or with a reducing gas, and
   iii) carbon monoxide alone or mixed with hydrogen, an alloy of (a) at least one metal selected from the group consisting of copper, rhodium, and palladium, and (b) at least one rare earth metal having a standard electrode potential of at least 0.8 volts negative with respect to the standard hydrogen electrode.

2. A process according to claim 1 wherein the alloy also contains at least one metal selected from aluminum and manganese.

3. A process according to claim 2 wherein the alloy contains aluminum and has a rare earth to aluminum weight ratio in the range of 10 to 0.2.

4. A process according to claim 2 wherein the alloy is an alloy of copper, rare earth, and manganese having a copper to rate earth weight ratio in the range of 0.5 to 2.0 and a manganese content of 0.5 to 15% by weight of the total alloy.

5. A process according to claim 4 wherein the alloy also contains 1-20% by weight of aluminum.

6. A process according to claim 1 wherein said reactive medium is a mixture of hydrogen and carbon monoxide.

7. A process according to claim 1 wherein the proportion of hydrogen to carbon oxides in the synthesis gas is such that the ratio of molar proportion of hydrogen, less the molar proportion of carbon dioxide, if any, to the total molar proportion of carbon oxides in the synthesis gas is in the range 0.5 to 2.

8. A process according to claim 1 wherein the synthesis is conducted at a temperature below 180° C.

9. A process according to claim 8 wherein the synthesis is conducted in a body of liquid substantially inert under the conditions of synthesis.

* * * * *